US00PP16000P2

(12) United States Plant Patent
Post

(10) Patent No.: US PP16,000 P2
(45) Date of Patent: Sep. 27, 2005

(54) ***CHRYSANTHEMUM* PLANT NAMED 'DELIROMA'**

(50) Latin Name: *Chrysanthemum×morifolium*
Varietal Denomination: Deliroma

(75) Inventor: Arie Gerard Post, 's-Gravenzande (NL)

(73) Assignee: Deliflor Royalties B.V., Maasdijk (NL)

( * ) Notice: Subject to any disclaimer, the term of this patent is extended or adjusted under 35 U.S.C. 154(b) by 33 days.

(21) Appl. No.: 10/919,003

(22) Filed: Aug. 16, 2004

(51) Int. Cl.[7] ..... A01H 5/00
(52) U.S. Cl. ..... Plt./286
(58) Field of Search ..... Plt./286

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Deliroma', characterized by its daisy-type inflorescences with red and yellow bi-colored ray florets; freely flowering habit; early and uniform flowering response; good postproduction longevity; and resistance to White Rust.

1 Drawing Sheet

Botanical classification/cultivar designation: *Chrysanthemum×morifolium* cultivar Deliroma.

BACKGROUND OF THE INVENTION

The present invention relates to a new and distinct cultivar of *Chrysanthemum* plant, botanically known as *Chrysanthemum×morifolium* and referred to by the name 'Deliroma'.

The new *Chrysanthemum* is the product of a planned breeding program conducted by the Inventor in 's Gravenzande, The Netherlands. The objective of the breeding program is to create new vigorous cut *Chrysanthemum* cultivars with interesting inflorescence forms and attractive floret coloration.

The new *Chrysanthemum* originated from a cross-pollination on Mar. 24, 2000 in 's Gravenzande, The Netherlands, of a proprietary seedling selection of *Chrysanthemum×morifolium* identified as code number DB7661, not patented, as the female, or seed, parent with a proprietary seedling selection of *Chrysanthemum×morifolium* identified as code number DB8696, not patented, as the male, or pollen, parent. The new *Chrysanthemum* was discovered and selected by the Inventor as a single plant within the progeny of the stated cross-pollination in a controlled environment in 's Gravenzande, The Netherlands.

Asexual reproduction of the new *Chrysanthemum* by terminal cuttings in a controlled environment in 's Gravenzande, The Netherlands since May 22, 2001, has shown that the unique features of this new *Chrysanthemum* are stable and reproduced true to type in successive generations.

BRIEF SUMMARY OF THE INVENTION

The cultivar Deliroma has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Deliroma'. These characteristics in combination distinguish 'Deliroma' as a new and distinct cultivar:

1. Daisy-type inflorescences with red and yellow bi-colored ray florets; typically grown as a spray-type.
2. Freely flowering habit.
3. Early and uniform flowering response.
4. Good postproduction longevity.
5. Resistant to White Rust.

Plants of the new *Chrysanthemum* can be compared to plants of the female parent selection. In side-by-side comparisons conducted in 's Gravenzande, The Netherlands, plants of the new *Chrysanthemum* differed from plants of the female parent selection in the following characteristics:

1. Plants of the new *Chrysanthemum* had shorter and thicker flowering stems than plants of the female parent selection.
2. Plants of the new *Chrysanthemum* and the female parent selection differed in ray floret coloration as plants of the female parent selection had purple-colored ray florets.
3. Plants of the new *Chrysanthemum* were resistant to White Rust whereas plants of the female parent selection were susceptible to White Rust.

Plants of the new *Chrysanthemum* can be compared to plants of the male parent selection. In side-by-side comparisons conducted in 's Gravenzande, The Netherlands, plants of the new *Chrysanthemum* differed from plants of the male parent selection in the following characteristics:

1. Plants of the new *Chrysanthemum* were more vigorous than plants of the male parent selection.
2. Plants of the new *Chrysanthemum* were more freely flowering than plants of the male parent selection.
3. Plants of the new *Chrysanthemum* and the male parent selection differed in ray floret coloration as plants of the male parent selection had pink and white bi-colored ray florets.

Plants of the new *Chrysanthemum* can be compared to plants of the *Chrysanthemum* cultivar Repulse, not patented. In side-by-side comparisons conducted in 's Gravenzande, The Netherlands, plants of the new *Chrysanthemum* differed primarily from plants of the cultivar Repulse in the following characteristics:

1. Plants of the new *Chrysanthemum* had thicker leaves than plants of the cultivar Repulse.

2. Plants of the new *Chrysanthemum* were more freely flowering than plants of the cultivar Repulse.
3. Plants of the new *Chrysanthemum* had more ray florets per inflorescence than plants of the cultivar Repulse.
4. Plants of the new *Chrysanthemum* and the cultivar Repulse differed in ray floret coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Deliroma'.

The photograph at the bottom of the sheet is a close-up view of the lower and upper surfaces of typical inflorescences and typical leaves of 'Deliroma'.

DETAILED BOTANICAL DESCRIPTION

In the following description, color references are made to The Royal Horticultural Society Colour Chart, 1995 Edition, except where general terms of ordinary dictionary siginificance are used. The aforementioned photographs and following observations and measurements describe plants grown during the winter and early spring in 's Gravenzande, The Netherlands, under commercial practice in a glass-covered greenhouse. Plants were initially given long day/short night treatments followed by short day/long night treatments to induce flower initiation and development. During the production of the plants, day and night temperatures averaged 19° C. and light levels were about 4,000 lux. Plants were grown as spray-types and were about ten weeks from planting when the photographs and the description were taken.

Botanical classification: *Chrysanthemum×morifolium* cultivar Deliroma.

Commercial classification: Daisy-type *Chrysanthemum* typically grown as a spray-type cut flower.

Parentage:

*Female, or seed, parent.*—Proprietary seedling selection of *Chrysanthemum×morifolium* identified as code number DB7661, not patented.

*Male, or pollen, parent.*—Proprietary seedling selection of *Chrysanthemum×morifolium* identified as code number DB8696, not patented.

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 10 days at 20° C.

*Time to produce a rooted cutting, winter.*—About 14 days at 18° C.

*Root description.*—Fine and freely branching; white in color.

Plant description:

*Appearance.*—Herbaceous daisy-type cut *Chrysanthemum*; typically grown as a spray-type; erect and strong flowering stems.

*Growth rate.*—Moderate; moderately vigorous.

*Flowering stem description.*—Length: About 70 cm. Diameter: About 6 mm. Strength: Strong. Aspect: Erect. Color: 146B.

*Foliage description.*—Arrangement: Alternate. Length: About 7.5 to 10.5 cm. Width: About 4.5 to 8 cm. Apex: Mucronate. Base: Obtuse. Margin: Pinnately lobed; serrate. Texture, upper and lower surface: Slightly pubescent. Petiole length: About 2.5 to 3.5 cm. Color: Developing foliage, upper surface: 137A. Developing foliage, lower surface: Between 137C and 147B. Fully expanded foliage, upper surface: Closest to 147A. Fully expanded foliage, lower surface: Between 137C and 147B. Venation, upper surface: 147B. Venation, lower surface: 146B. Petiole, upper and lower surfaces: 146C.

Inflorescence description:

*Appearance.*—Daisy-type inflorescence form with spatulate-shaped ray florets. Inflorescences borne on terminals above foliage. Disk and ray florets develop acropetally on a capitulum. Inflorescences not fragrant, Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 50 days later. Early and uniform flowering response.

*Postproduction longevity.*—Cut inflorescences will maintain good substance and form for about three weeks.

*Quantity of inflorescences per flowering stem.*—About 30 to 35 inflorescences per flowering stem.

*Inflorescence size.*—Diameter: About 5.5 to 6.5 cm. Depth (height): About 2.5 to 3 cm. Diameter of disc: About 8 mm.

*Inflorescence buds.*—Length: About 7 mm. Diameter: About 1 cm. Shape: Globular. Color: 146B.

*Ray florets.*—Length: About 3.5 cm. Corolla tube length: About 1.75 cm. Width: About 1 cm. Shape: Spatulate. Apex: Acute to rounded, emarginate. Base: Fused. Margin: Entire. Texture, upper and lower surfaces: Smooth, glabrous; satiny. Number of ray florets per inflorescence: About 20 in a single whorl. Color: When opening, upper surface: Towards the apex, 53A; towards the base, 5A. When opening, lower surface: 6C underlain with 59D. Fully opened, upper surface: Towards the apex, 53A; towards the base, 5A. Fully opened, lower surface: 5C underlain with 59D.

*Disc florets.*—Shape: Tubular. Length: About 7 mm. Width: About 1 mm. Number of disc florets per inflorescence: About 160 to 170. Color: 145C; towards the apex, 153C.

*Peduncles.*—Length, terminal peduncle: About 1.5 cm. Length, fourth peduncle: About 4 cm. Diameter: About 2 mm. Strength: Moderately strong. Texture: Pubescent. Color: 146B.

*Reproductive organs.*—Androecium: Present on disc florets only. Anther color: 14A. Pollen color: 14A. Gynoecium: Present on both ray and disc florets.

*Seed/fruit.*—Seed and fruit production has not been observed.

Disease/pest resistance: Plants of the new *Chrysanthemum* have been observed to be resistant to White Rust. Resistance to known *Chrysanthemum* pests and other pathogens has not been obsrved on plants of the new *Chrysanthemum.*

It is claimed:

1. A new and distinct cultivar of *Chrysanthemum* plant named 'Deliroma', as illustrated and described.

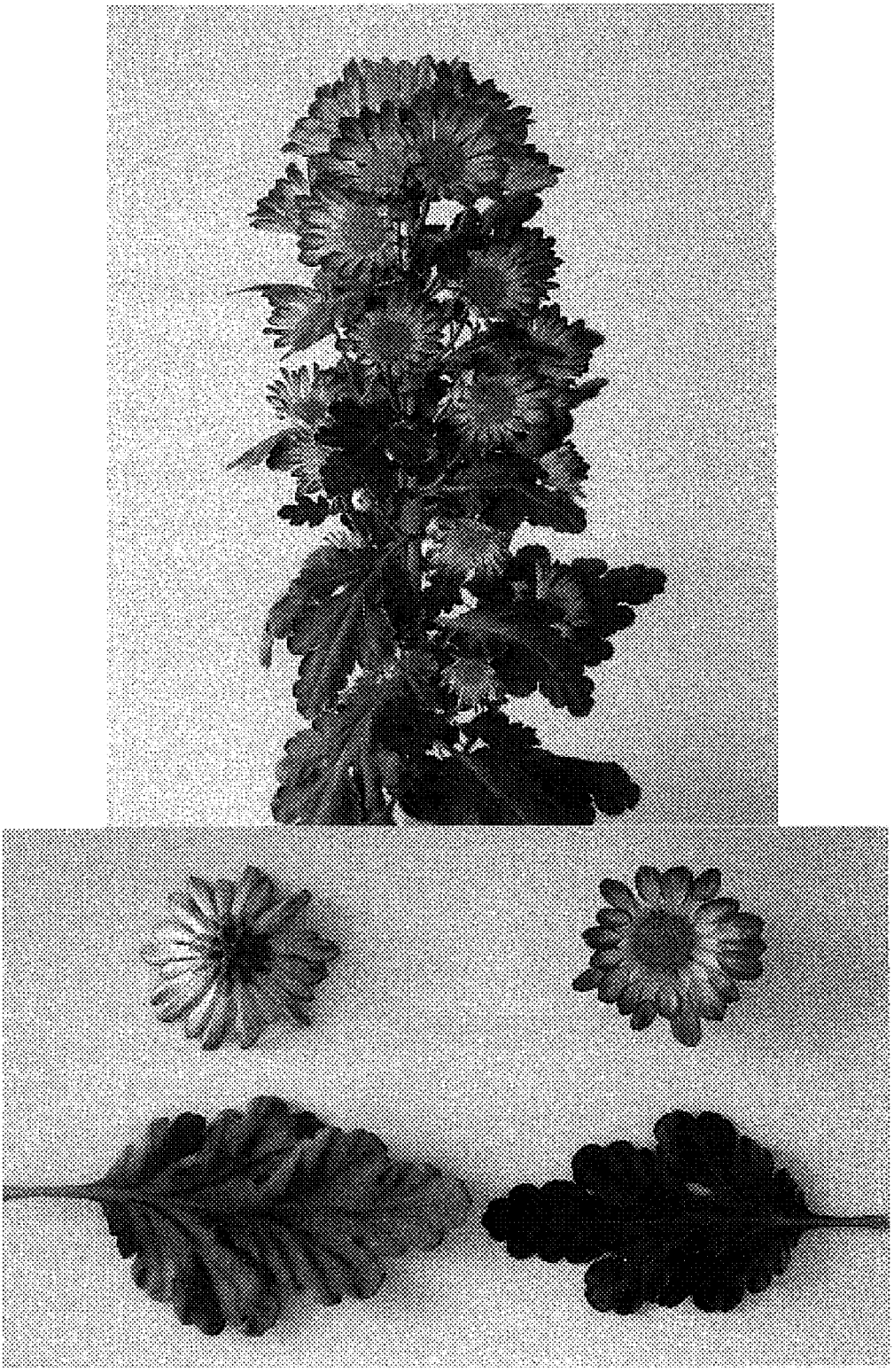

* * * * *